(12) United States Patent
Jugl et al.

(10) Patent No.: US 9,186,467 B2
(45) Date of Patent: Nov. 17, 2015

(54) NEEDLE ASSEMBLY COVER

(75) Inventors: Michael Jugl, Frankfurt am Main (DE); Axel Teucher, Frankfurt am Main (DE)

(73) Assignee: Sanofi-Aventis Deutschland GMBH, Frankfurt am Main ( * ) Notice: Subject to any disclaimer, the term of this patent is extended or adjusted under 35 U.S.C. 154(b) by 0 days.

(21) Appl. No.: 14/122,904

(22) PCT Filed: May 29, 2012

(86) PCT No.: PCT/EP2012/059987
§ 371 (c)(1),
(2), (4) Date: Nov. 27, 2013

(87) PCT Pub. No.: WO2012/163890
PCT Pub. Date: Dec. 6, 2012

(65) Prior Publication Data
US 2014/0094758 A1 Apr. 3, 2014

(30) Foreign Application Priority Data
May 30, 2011 (EP) .................................... 11168011

(51) Int. Cl.
*A61M 5/24* (2006.01)
*A61M 5/32* (2006.01)
*A61M 5/34* (2006.01)

(52) U.S. Cl.
CPC ........... *A61M 5/3213* (2013.01); *A61M 5/3202* (2013.01); *A61M 5/347* (2013.01); *A61M 2205/43* (2013.01); *A61M 2205/581* (2013.01); *A61M 2205/582* (2013.01)

(58) Field of Classification Search
CPC ................... A61M 2205/43; A61M 2205/581; A61M 2205/582; A61M 5/347
USPC .................................................. 604/206, 240
See application file for complete search history.

(56) References Cited

U.S. PATENT DOCUMENTS

| 3,967,621 A | 7/1976 | Schwarz |
| 4,747,835 A | 5/1988 | Sandhaus |
| 2009/0069753 A1* | 3/2009 | Ruan et al. ..................... 604/192 |

FOREIGN PATENT DOCUMENTS

| DE | 19915272 | * 10/2000 |
| DE | 19915272 A1 | 10/2000 |
| EP | 2039384 A2 | 3/2009 |

* cited by examiner

*Primary Examiner* — Kevin C Sirmons
*Assistant Examiner* — Deanna K Hall
(74) *Attorney, Agent, or Firm* — Fish & Richardson P.C.

(57) ABSTRACT

Described is a needle assembly system comprising a needle assembly including a needle and a needle support, and a cover including a distal portion adapted to house at least a distal end of the needle and a proximal portion adapted to house the needle support. The proximal portion includes a first portion and a second portion. The first portion has a first inner diameter substantially equal to an outer diameter of the needle support and the second portion has a second inner diameter greater than the diameter of the needle support.

7 Claims, 2 Drawing Sheets

NEEDLE ASSEMBLY COVER

CROSS REFERENCE TO RELATED APPLICATIONS

The present application is a U.S. National Phase Application pursuant to 35 U.S.C. §371 of International Application No. PCT/EP2012/059987 filed May 29, 2012, which claims priority to European Patent Application No. 11168011.2 filed May 30, 2011. The entire disclosure contents of these applications are herewith incorporated by reference into the present application.

FIELD OF INVENTION

The invention relates to a cover for a needle assembly, which is used with an injection device such as, for example, a pen injector or an auto-injector.

BACKGROUND

Patients suffering from diseases like diabetes have to frequently self-administer injections. Injection devices like auto-injectors or pen injectors have been developed to facilitate self-administering injections. Typically, such injection devices are re-usable and refitted with sterile injection needle assemblies to minimize the risk of infections.

A conventional needle assembly is coupled to an injection device by a threaded engagement. However, patients typically over-tighten the needle assembly when coupling it to the injection device making removal of the needle assembly difficult. Difficulties in removing the needle assembly can lead to needle-stick injuries and infection. Thus, there is a need for an improved means by which to couple and remove the needle assembly to/from an injection device.

SUMMARY

It is an object of the present invention to provide a needle assembly cover for a needle assembly which is used with an injection device.

In an exemplary embodiment, a needle assembly system comprises a needle assembly including a needle and a needle support, and a cover including a distal portion adapted to house at least a distal end of the needle and a proximal portion adapted to house the needle support. The proximal portion includes a first portion and a second portion. The first portion has a first inner diameter substantially equal to an outer diameter of the needle support and the second portion has a second inner diameter greater than the diameter of the needle support.

In an exemplary embodiment, a first inner surface of the first portion frictionally engages the needle support. A second inner surface of the second portion does not frictionally engage the needle assembly. The second inner surface includes at least one projection, and an outer surface of the needle support includes at least one groove. Engagement of the at least one projection with the at least one groove provides at least one of an audible feedback and a tactile feedback.

In an exemplary embodiment, the cover includes at least one extension extending proximally of the proximal portion. The at least one extension is adapted to abut an injection device.

In an exemplary embodiment, the proximal portion is elastically deformable.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

Corresponding parts are marked with the same reference symbols in all figures.

DETAILED DESCRIPTION

Figure 1:
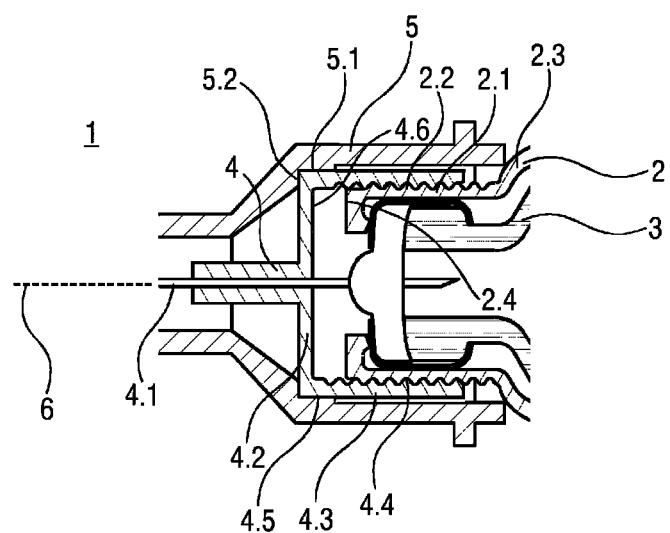
FIG. 1 shows a sectional view of a section of a needle assembly cover according to an exemplary embodiment of the present invention.

As shown in FIG. 1, a needle assembly system 1 comprises a needle assembly 4 and a cover 5 for the needle assembly 4. The needle assembly 4 may be coupled to an injection device 2 such as, for example, a pen injector or an auto-injector. The injection device 3 contains a medicament module 3, such as a cartridge or a pre-filled syringe.

The needle assembly 4 may include a needle support 4.2 and a needle 4.1. The needle 4.1 may include a proximal tip for piercing a septum on the medicament module 3 and a distal end for piercing an injection site. The needle support 4.2 may be cylindrical and have an inner threaded surface 4.4 adapted to mate with an outer threaded surface 2.2 on a distal end 2.1 of the injection device 2. The needle 4.1 may be disposed along a longitudinal axis 6 of the needle assembly 4.

In an exemplary embodiment, the cover 5 for the needle assembly 4 includes a distal portion, a middle portion and a proximal portion. The distal portion may be cylindrical and adapted to house the distal end of the needle 4.1. The distal portion of the cover 5 may have a closed distal end to prevent exposure of the distal end of the needle 4.1. The middle portion of the cover 5 may have a frusto-conical shape, increasing in diameter from distal to proximal ends. A proximal end of the middle portion may include a stop face 5.2 formed an inner surface thereof. The stop face 5.2 may include or more projections or annular surface which project into an interior of the cover 5. The stop face 5.2 may abut a distal face 4.5 of the needle support 4.2 to prevent the needle support 4.2 from moving distally within the cover 5 past the stop face 5.2

In an exemplary embodiment, the proximal portion of the cover 5 may be cylindrical, having a substantially constant outer diameter along its length. The proximal portion may have a first portion 5.1 with a first inner diameter which is substantially equal to an outer diameter of the needle support 4.2. Thus, the first portion 5.1 of the proximal portion of the cover 5 may frictionally engage the needle support 4.2. The proximal portion may have a second portion with a second inner diameter which is greater than the outer diameter of the needle support 4.2. Thus, the cover 5 may rotate relative to the needle support 4 when the needle support 4.2 is in the cover 5 but does not engage the first portion 5.1.

As shown in FIG. 1, the needle assembly 4 is in a first position (e.g., a distal position) within the cover 5 when the needle assembly 4 first engages the injection device 2. When the needle assembly 4 first engages the injection device 2, one or more extensions extending proximally from a proximal end 2.6 of the cover 5 may abut a shoulder 2.3 on the injection device 2. Thus, in this exemplary embodiment, the cover 5 may not move axially when the needle assembly 4 is being engaged to (or disengaged from) the injection device 2. In other exemplary embodiments, the cover 5 may move axially until the proximal end of the cover 5 abuts the shoulder 2.3.

In the first position, the distal face 4.5 of the needle support 4.2 abuts the stop face 5.2 of the middle portion of the cover 5. When the needle support 4.2 engages the distal end 2.1 of the injection device 2, the cover 5 may be rotated relative to the injection device 2, and due to the frictional engagement between the first portion 5.1 of the proximal portion of the cover 5 and the needle support 4.2, the needle support 4.2 may be temporarily, positionally fixed relative to the cover 5. As the inner threaded surface 4.4 of the needle support 4.2 engages the outer threaded surface 2.2 of the injection device 2, the needle support 4.2 may be axially advanced in a proximal direction toward the injection device 2.

Figure 2:
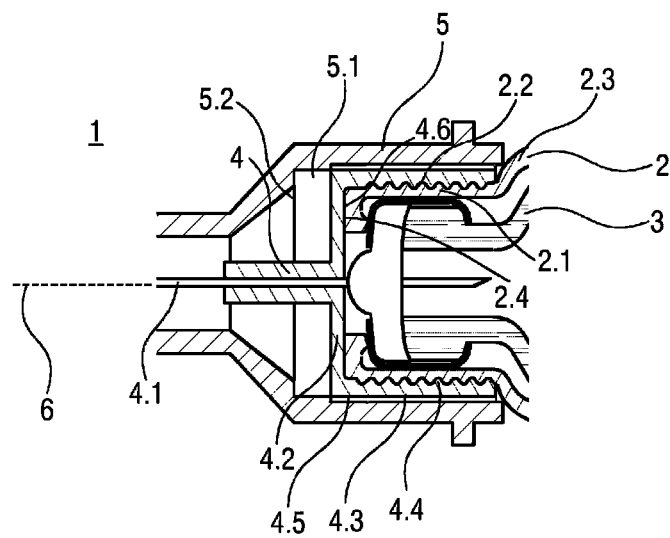
FIG. 2 shows a sectional view of a section of a needle assembly cover according to an exemplary embodiment of the present invention.

FIG. 2 shows an exemplary embodiment of the needle assembly 4 in a second position (e.g., proximal position) within the cover 5 after one or more rotations of the cover 5 relative to the injection device 2. In the second position, the needle support 4.2 has disengaged from the first portion 5.1 of the proximal portion of the cover 5 and is in the second portion. Because the second portion has the second diameter greater than the outer diameter of the needle support 4.2, further rotation of the cover 5 may not result in rotation of the needle assembly 4. Thus, in the second position, the needle assembly 4 has properly engaged the injection device 2 (e.g., a distal face 2.4 of the injection device 2 abuts a distal end of the needle support 4.2 and a proximal end 4.7 of the needle assembly 4 abuts the shoulder 2.3), but the radial separation between the cover 5 and the needle support 4.2 prevents over-tightening of the needle assembly 4 to the injection device 2.

In an exemplary embodiment, at least a portion of an outer surface 4.3 of the needle support 4.2 may have a plurality of grooves formed therein, and the inner surface of the second portion of the proximal portion of the cover 5 may have one or more projections formed thereon. When the needle assembly 4 is in the second position within the cover 5, further rotation of the cover 5 may cause the one or more projections to intermittently abut the plurality of grooves, thereby providing an audible ("clicking") feedback and/or a tactile feedback. The audible and/or tactile feedbacks may indicate to the patient that the needle assembly 4 has been properly secured to the injection device 2 and further rotation of the cover 5 is neither necessary nor desirable.

To remove a used needle assembly 4 from the injection device 2, the cover 5 may be placed on the needle assembly 4. Because the needle assembly 4 is in the second position and the cover 5 may rotate relative to the needle assembly 4, the patient may be required to pinch the proximal portion of the cover 5 so that the cover 5 engages the needle support 4.2.

Thus, at least the proximal portion of the cover 5 may be elastically deformable to allow for squeezing. After a few pinched rotations of the cover 5, the needle support 4.2 may be advanced axially within the cover 5 into engagement with the first portion 5.1 of the proximal portion of the cover 5 and pinching the cover 5 may no longer be necessary to disengage the needle assembly 4 from the injection device 2.

Figure 3:
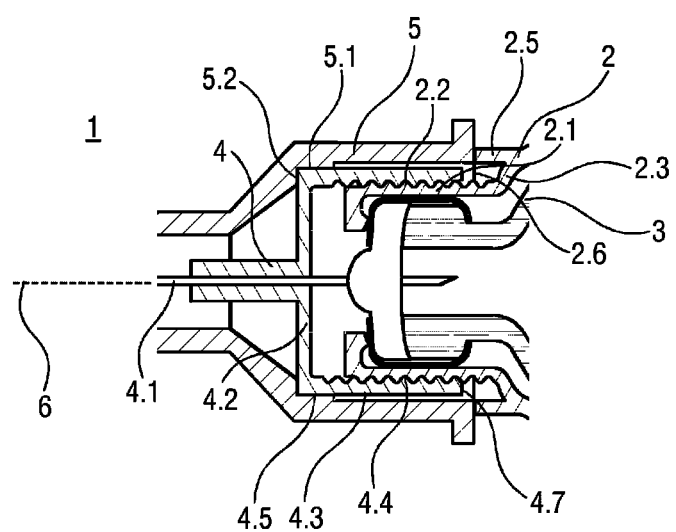
FIG. 3 shows a sectional view of a section of a needle assembly cover according to an exemplary embodiment of the present invention.

FIG. 3 shows another exemplary embodiment of a needle assembly system 1 according to the present invention. In this exemplary embodiment, one or more protrusions 2.5 are formed on the shoulder 2.3 of the injection device 2. The protrusions 2.5 abut the proximal portion of the cover 5 and prevent axial movement of the cover 5 relative to the injection device 2 in a proximal direction.

Those of skill in the art will understand the modifications (additions and/or removals) of various components of the device and/or system and embodiment described herein may be made without departing from the full scope and spirit of the present invention, which encompass such modifications and any and all equivalents thereof.

The invention claimed is:

1. A needle assembly system comprising:
a needle assembly including a needle and a needle support;
a cover including a distal portion adapted to house at least a distal end of the needle and a proximal portion adapted to house the needle support,
wherein the proximal portion includes a first portion and a second portion, wherein the first portion has a first inner diameter substantially equal to an outer diameter of the needle support such that the first portion of the proximal portion of the cover is frictionally engaged with the needle support in a first position and the second portion has a second inner diameter greater than the diameter of the needle support such that there is radial separation between the cover and the needle support in a second position, wherein the second portion of the proximal portion has a length greater than or equal to a length of the needle support, wherein the needle support is configured to be axially advanced from the first position to the second position such that a proximal end of the needle assembly does not extend past a proximal end of the cover.

2. The needle assembly system according to claim 1, wherein a first inner surface of the first portion frictionally engages the needle support.

3. The needle assembly system according to claim 2, wherein a second inner surface of the second portion does not frictionally engage the needle assembly.

4. The needle assembly system according to claim 3, wherein the second inner surface includes at least one projection, and an outer surface of the needle support includes at least one groove.

5. The needle assembly system according to claim 4, wherein engagement of the at least one projection with the at least one groove provides at least one of an audible feedback and a tactile feedback.

6. The needle assembly system according to claim 1, wherein the cover includes at least one extension extending proximally of the proximal portion, wherein the at least one extension is adapted to abut an injection device.

7. The needle assembly system according to claim 1, wherein the proximal portion is elastically deformable.

* * * * *